(12) United States Patent
Bittman

(10) Patent No.: US 9,368,014 B1
(45) Date of Patent: Jun. 14, 2016

(54) PATIENT ACTIVITY SIGNATURE ANALYSIS

(71) Applicant: Barry B. Bittman, Meadville, PA (US)

(72) Inventor: Barry B. Bittman, Meadville, PA (US)

(*) Notice: Subject to any disclaimer, the term of this patent is extended or adjusted under 35 U.S.C. 154(b) by 0 days.

(21) Appl. No.: 14/518,186

(22) Filed: Oct. 20, 2014

Related U.S. Application Data

(60) Provisional application No. 61/892,632, filed on Oct. 18, 2013.

(51) Int. Cl.
G08B 1/08 (2006.01)
G08B 21/04 (2006.01)
G06F 19/00 (2011.01)
G08B 5/36 (2006.01)

(52) U.S. Cl.
CPC ........ *G08B 21/0453* (2013.01); *G06F 19/3406* (2013.01); *G08B 5/36* (2013.01)

(58) Field of Classification Search
CPC ............................ G08B 21/04; G08B 21/0446
USPC ........... 340/539.12, 573.1, 522; 600/301, 595
See application file for complete search history.

(56) References Cited

U.S. PATENT DOCUMENTS

| 8,180,440 B2* | 5/2012 | McCombie | A61B 5/02028 600/513 |
| 9,019,099 B2* | 4/2015 | Fox | A61B 5/0022 128/903 |
| 2010/0262045 A1* | 10/2010 | Heaton | A61B 5/1112 600/595 |
| 2012/0229634 A1* | 9/2012 | Laett | G08B 21/0476 348/143 |
| 2015/0206409 A1* | 7/2015 | Visvanathan | A61B 5/002 340/573.1 |

* cited by examiner

*Primary Examiner* — Toan N Pham
(74) *Attorney, Agent, or Firm* — Brian Clarke; Clarke IP Law

(57) ABSTRACT

Tools, strategies, and techniques are provided for remote, early detection of patient health condition based on deviations from established patterns of patient movement or other activity. Once established, a patient activity signature can be compared to observed patient behavior to detect unacceptable or unexpected deviations from the activity signature. Deviation from a patient movement signature can be detected and can cause an alert or other notification to be generated or communicated to a physician, for example, or other appropriate health care providers.

22 Claims, 6 Drawing Sheets

Data Analysis System

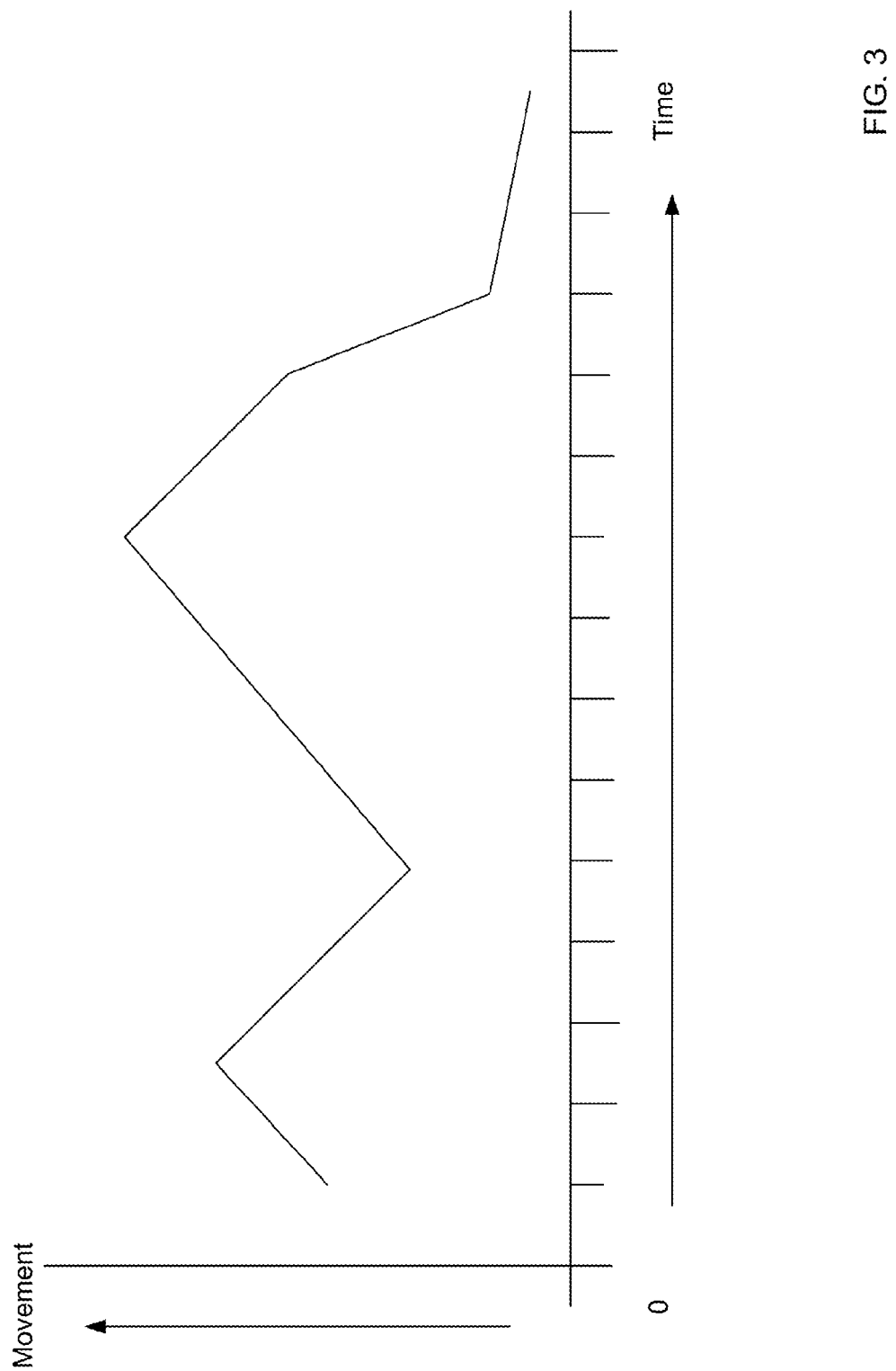

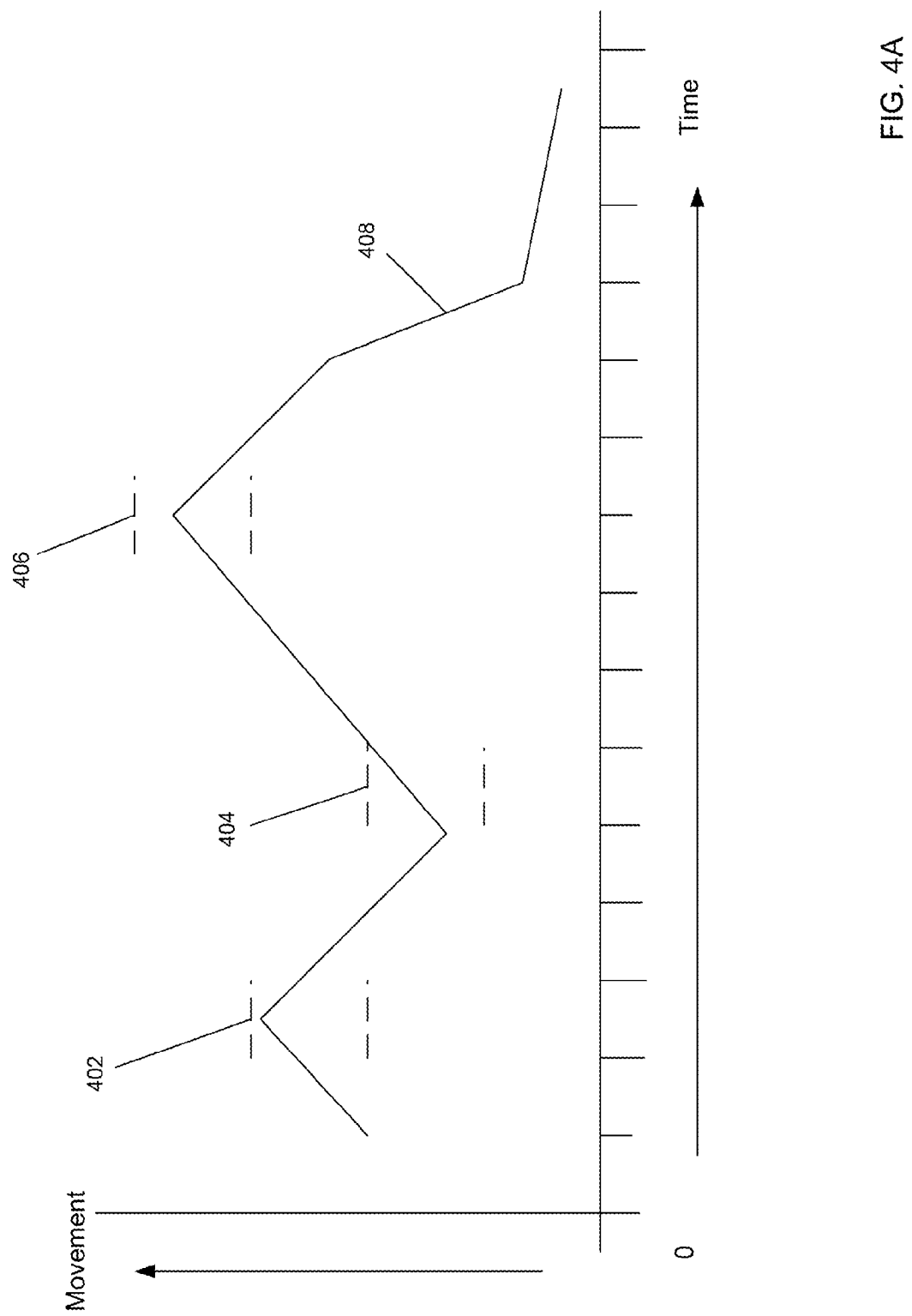

| Patient | Alert Level | | | Action Taken | Notes |
|---|---|---|---|---|---|
| | Low | Medium | High | | |
| | | | | | |
| | | | | | |
| | | | | | |
| | | | | | |
| | | | | | |
| | | | | | |
| | | | | | |

PATIENT ACTIVITY SIGNATURE ANALYSIS

CROSS-REFERENCE TO RELATED APPLICATION/PRIORITY CLAIM

The present application claims the benefit of U.S. provisional patent application Ser. No. 61/892,632, filed on Oct. 18, 2013, the entirety of which is hereby incorporated by reference.

BACKGROUND

The cost of health care has risen to unsustainable levels. In the United States, approximately 5% of the population utilizes 49% of all health care resources, and many of these patients have multiple comorbidities and suffer from chronic conditions. It has been estimated by the Institute of Medicine that $690 billion or roughly one third of the United States health care budget represents wasted spending. From a financial perspective, the United States health care system is evolving from a fee-for-service system to a quality system based primarily on patient outcomes. One of the keys to this evolving global payment system is preventing unnecessary spending, including avoiding costly hospital admissions and readmissions.

A formidable underlying issue affecting health care delivery is early symptom recognition associated with suboptimal communication between patients and their health care providers. Inordinate delays in reporting symptomatic changes can interfere with efficient diagnosis, proper evaluation and effective treatment. Symptom exacerbations not detected in the early stages, and resultant reporting delays to physicians or care coordination teams, can result in higher levels of disease severity and costly hospital admissions and readmissions.

Population health management strategies focus on caring for individuals within a community-based, continuous care no-charge system. Care extends seamlessly from in-patient hospitalization through rehabilitation, long-term care, and into home environments. Patient monitoring is important throughout these phases of care yet can be especially challenging, cumbersome and expensive, while also not being sufficiently effective. For example, fall alert monitoring systems can provide valuable information about a patient's condition. However, these systems are designed for after-the-fact episodes, such as after the patient has already fallen and potentially sustained injuries, and are therefore ineffective at predicting a patient fall in advance.

In response to the issues described above, the inventor has recognized a need to provide a health care early warning system, among other enhanced tools, strategies, and techniques that can help health care providers and other practitioners to monitor patient condition and to maximize patient care.

BRIEF DESCRIPTION OF FIGURES

The utility of the embodiments of the invention will be readily appreciated and understood from consideration of the following description of the embodiments of the invention when viewed in connection with the accompanying drawings, wherein:

FIG. 3 includes a graphical representation of a patient activity signature generated in accordance with various embodiments of the invention;

FIG. 4A includes a graphical representation of the patient activity signature of FIG. 3 including select movement deviation bands;

DESCRIPTION

In various embodiments, the invention offers tools, strategies, and techniques for remote, early detection of disease onset or exacerbation based on deviations from established patterns of patient movement or other activity. The invention may use a variety of analytical tools, such as neural networking or machine learning algorithms to generate a movement pattern or activity signature for a patient. Once established, a patient activity signature can be compared to observed patient behavior to detect unacceptable or unexpected deviations from the activity signature. Deviation from a patient movement signature can be detected and can cause an alert or other notification to be generated or communicated to a physician, for example, or other appropriate health care providers.

The inventor has discovered many different scenarios in which it is useful to apply a predictive analysis with a patient activity signature, such as to facilitate intervention on the patient's behalf to provide health care. For example, a patient with poorly controlled diabetes will walk less due to hypoglycemic or hyperglycemic changes that result in gait instability and/or dizziness. Patients with conditions such as worsening CHF or COPD will awaken more frequently at night. In another example, a patient with an exacerbation or nuance of pneumonia will tend to stay in bed longer. A person with CVD who is experiencing exertional dyspnea might take shorter walks. A person on dialysis with fluid overload or electrolyte imbalance will likely take more frequent naps. In another example, a person experiencing medication side effects such as fatigue will tend to go to bed earlier in the evening. Also, in still another example, a patient who suffers a hip fracture secondary to a fall often experiences gait instability with changes in ambulation prior to the fall. In each of these scenarios, a proper predictive analysis can be useful to provide an advance warning to health care providers of changing or deteriorating patient conditions.

Figure 1:
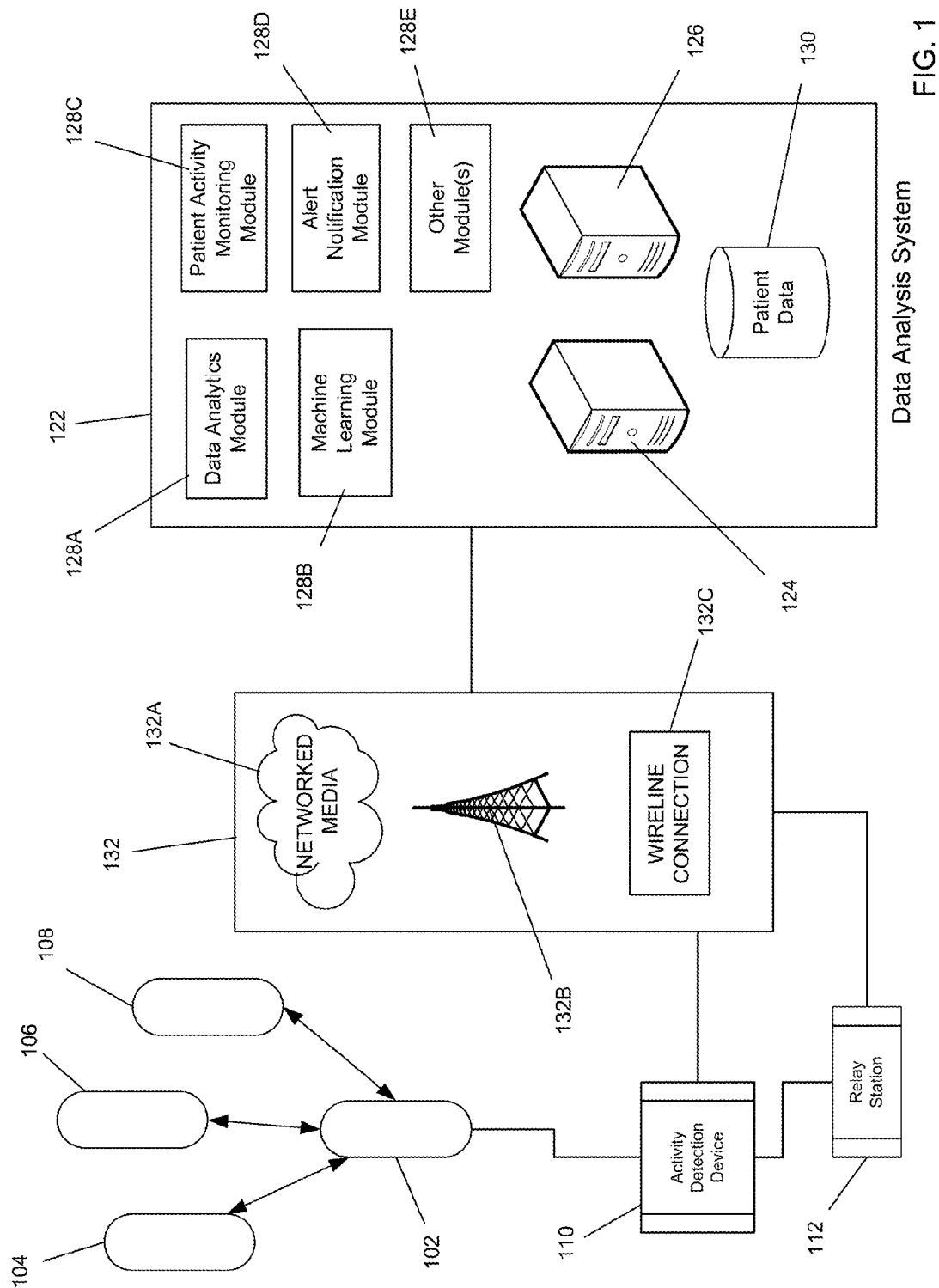
FIG. 1 includes an example of a system architecture structured and programmed in accordance with various embodiments of the invention.

With reference to FIG. 1, a patient 102 engages in movement or other activity associated with different locations or positions 104, 106, 108. An activity detection device 110 may be operatively associated with the patient 102 and may be programmed to collect various data representative of the movement or activity of the patient 102. The device 110 may be embodied as a low energy drain, rechargeable, wearable data collection device, for example. The device 110 can be worn on the neck, arm, wrist, or other convenient location on the body of the patient 102. In various embodiments, the device 110 may include a plurality of sensors, such as motion sensors, tilt sensors, inertia sensors, global positioning systems (GPS), accelerometers, and/or many others. In certain embodiments, other types of sensors (e.g., non-motion sensors) may be used to augment the accuracy of the motion signature deviation data. Such other types of sensors may include heart rate sensors, blood pressure sensors, breathing or oxygen sensors, or other kinds of sensors which detect and transmit signals representative of the physiological condition of the patient 102, for example.

In certain embodiments, the device 110 may be a smart phone, mobile phone, electronic tablet, or another type of wireless-enabled device. The device 110 may include a wireless transmitter, for example, for collecting and sending data to a relay station 112 for performing Internet data uploads to a data analysis system 122. The relay station 112 may be located in an environment around the patient 102 and may be programmed to receive data from the device 110 with subsequent transfer via the Internet of secure encrypted data to analytic software, algorithms, and other processes of the system 122. In certain embodiments, the device 110 may communicate, collect data, and/or transmit data with or without assistance from the relay station 112.

In the example shown, the system 122 may include a web server 124 programmed to receive communicated patient data and/or to host one or more web sites. One or more websites configured, generated, and/or displayed by the web server 124 may be based on a LAMP stack (i.e., a combination of components derived from Linux, Apache, MySQL, and PHP), for example. The system 122 may also include an application server 126 programmed to process transactions associated with receiving, accessing, or storing patient activity or patient movement data. In various embodiments, the system 122 may include various modules 128A-128E programmed for executing computer-based instructions for directing a processor or computer system to perform different tasks or functions within the system 122. A data analytics module 128A may be programmed for receiving and processing data associated with patient activity or movement related data, including generating various patient activity signatures, for example. The data analytics module 128A may work in connection with a machine learning module 128B to assist with the process of determining patterns associated with patient behavior that can be converted into predictive models such as patient activity signatures. A patient activity monitoring module 128C may be programmed for comparing generated patient activity signatures against actual patient activity, movement, or motion data to determine whether a deviation from the patient activity signature has occurred, for example. An alert notification module 128D may be programmed to generate notifications, such as when actual patient movement data is outside standard tolerances for a given patient activity signature, for example. Also, other modules 128E may be provided in the system 122 to perform other types of tasks, functions, and/or data analyses. In various embodiments, one or more databases 130 or other types of data storage media may be provided in the system 122 for storing and retrieving patient activity data and/or patient activity signature data, for example.

Figure 2:
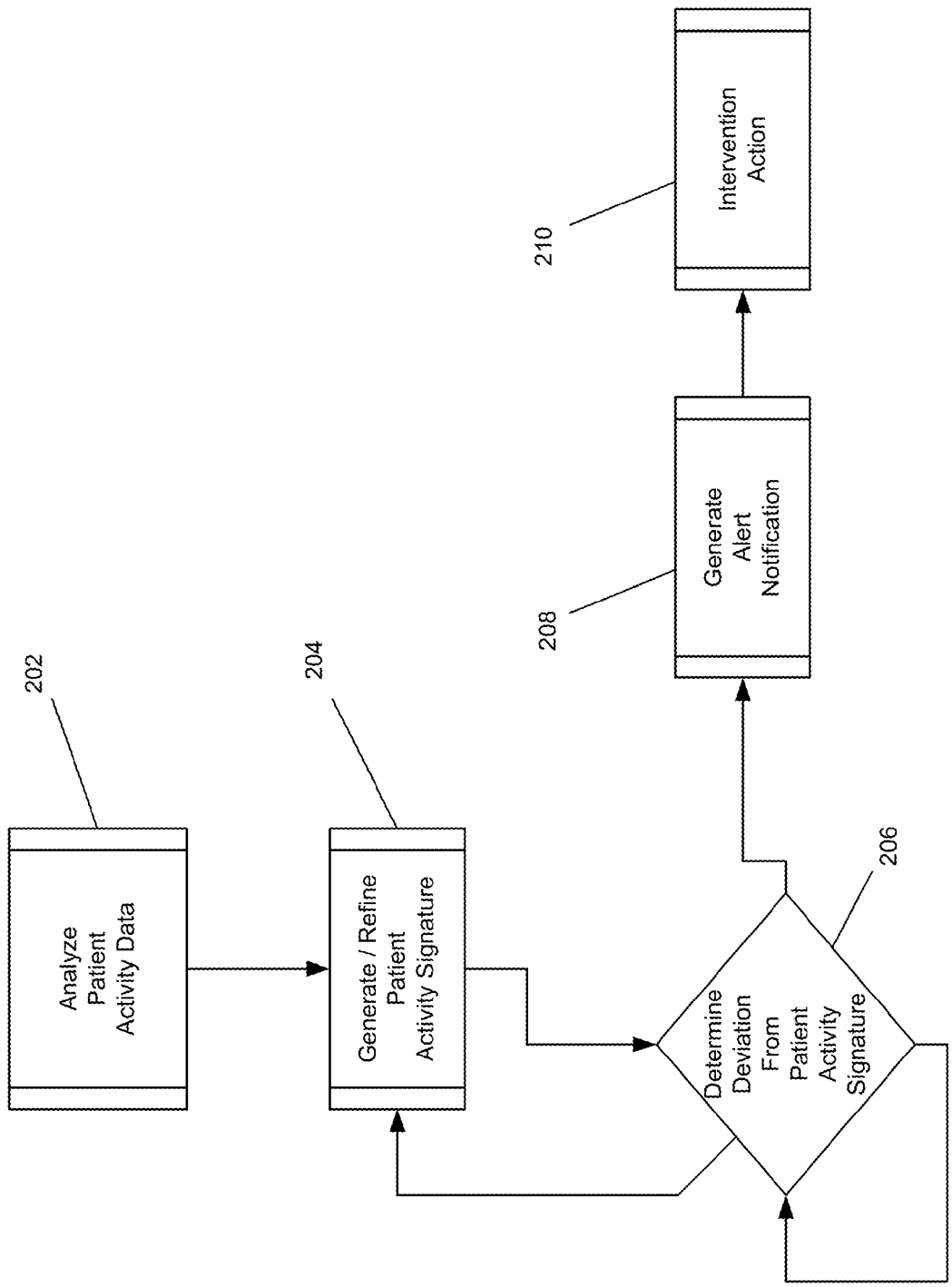
FIG. 2 includes a process flow diagram showing one example of collecting and processing patient activity signature data in accordance with various embodiments of the invention.

With reference to FIG. 2, communicated raw data can be received, deciphered and processed by the data analysis system 122 at step 202 using a plurality of statistical methods and algorithms. Motion can be quantified and analyzed in terms of magnitude, duration, frequency and temporal occurrence, among other factors. Motion can be detected and converted to the degree of movement in specified intervals, e.g., hourly, daily, weekly, weekdays, weekends, or specific intervals such as sleep or wake periods. Data may be collected and analyzed in response to temporal occurrence including determining specifically when the motion occurs (e.g., time of morning, upon awakening or sleeping, sleep interruption, etc.) The data analytics module 128A and the machine learning module 128B can be programmed to refine patterns progressively over time at step 204 with the development of an epoch-based personalized activity signature or patient activity signature for each patient 102. An example of a graphical representation of a patient activity signature is shown in FIG. 3.

Figure 4B:
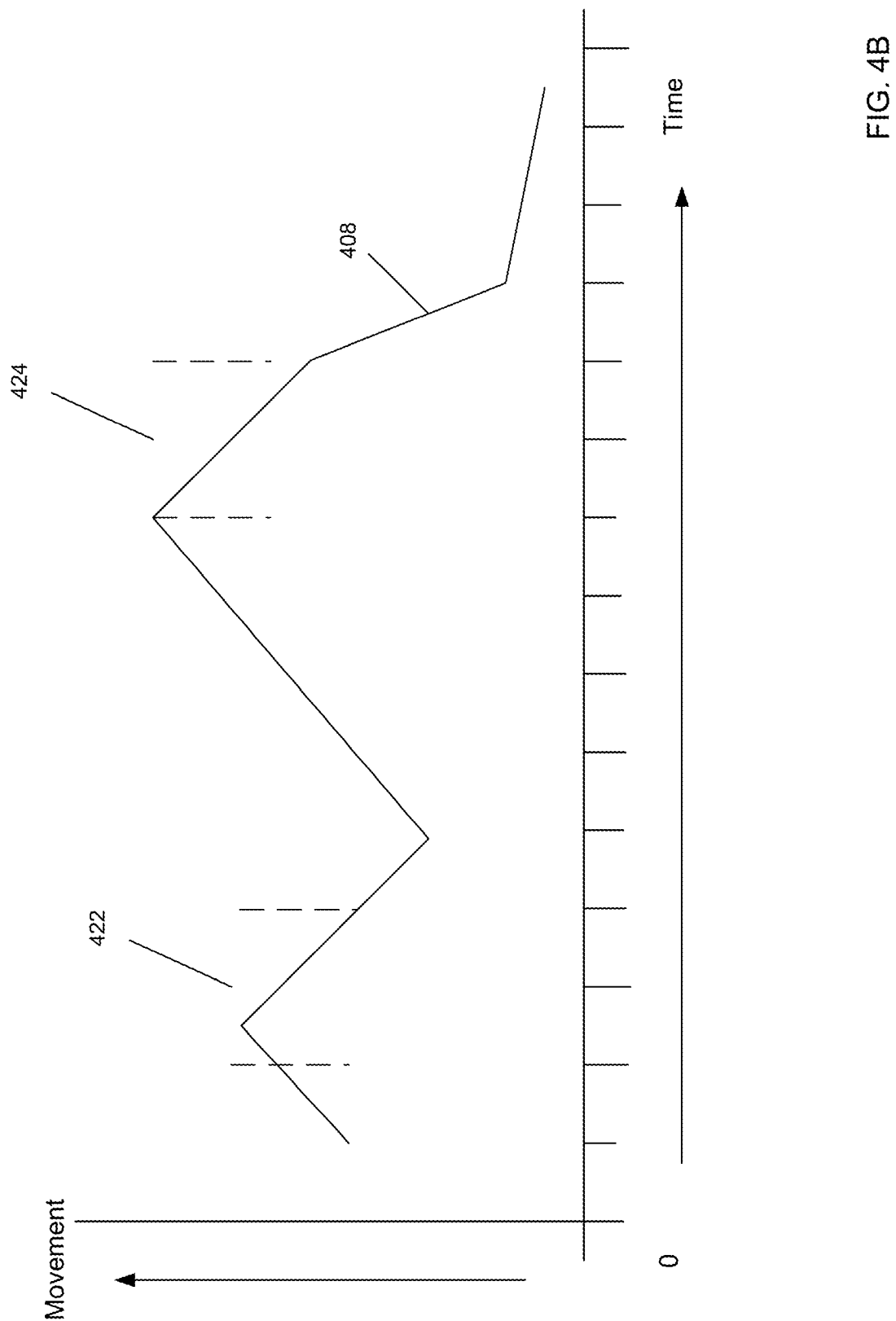
FIG. 4B includes a graphical representation of the patient activity signature of FIG. 3 including select temporal deviation bands; and, FIG. 5 includes an example of a dashboard screen that can be presented as an alert notification to a user in accordance with various embodiments of the invention.

In various embodiments, motion can be plotted (e.g., mathematically superimposed) via machine learning, for example, over time to create an evolving, progressively refined spectrum of activity (e.g., by magnitude, frequency, and/or duration). As the spectrum becomes refined, the data can be analyzed and deviations can be statistically determined by the patient activity monitoring module 128C at step 206, for example, to refine the patient activity signature and/or to signal a change in patient condition at step 208. As illustrated in the example of FIG. 4A, tolerance bands 402, 404, 406 can be established around one or more aspects of a patient activity signature 408 to determine deviations from the patient activity signature 408. In FIG. 4A, the tolerance bands 402, 404, 406 have been established with respect to deviations from an acceptable degree of movement by a patient (e.g., as measured quantitatively along the y-axis direction). For example, FIG. 4A can be used as a tool to understand whether the patient has moved an inordinate distance in the relevant time period. In another example, FIG. 4B illustrates how tolerance bands 422, 424 can be established with respect to deviations from an acceptable degree of the temporal aspects of movement (e.g., as quantified along the x-axis in terms of hours, days, day parts, or another time measurement). FIG. 4B can be used as a tool to understand whether the patient has initiated movement at a time that is earlier than expected or later than expected, such as movement occurring at 12:00 am instead of at 6:00 am when the patient normally rises from sleep, for example.

Deviations from individualized patterns can be detected and utilized to refine the evolving signature and/or to report significant departures from the progressively refined signature. The degree to which data matches or deviates from a progressively refined patient activity signature can be represented by green, amber, or red dashboard notifications, for example, through operation of the alert notification module 128D. For example, a "green" indicator may mean patient activity is within one standard deviation of an expected activity level; an "amber" indicator may mean patient activity is within two standard deviations of an expected activity level; and a "red" indicator may mean patient activity exceeds two standard deviations from expected activity level. Z scores and other statistical methods can be utilized by the data analytics module 128A and/or the activity monitoring module 128C, for example, to determine significant deviations from progressively established patterns. At step 210, intervention action may be taken by a physician or other health care providers in response to deviation in actual or observed patient movement or other activity from the patient activity signature.

In various embodiments, the sensitivity for alert generation and reporting purposes can be tunable and adjustable through tools provided within the system 122, such as the alert notification module 128D. For example, warnings or other alerts associated with patient activity or movement can be presented to a user with dashboard screens. Dashboards can be reviewed and monitored on a periodic basis, for example, and may present key indicators for each subject or patient such as a deviation in overall activity, deviation in timing of activity, and/or deviation in other life activity patterns (e.g., sleep interruptions). In the dashboard example shown in FIG. 5, a first column 502 includes a patient list and other columns 504, 506, 508 may be colored (respectively) green for "low" risk, amber for "medium" risk, or red for "high" risk corresponding to a current alert level for each patient. In certain embodiments, accessing alert data in the dashboard may launch a secondary screen that explains the nature of or reason for the alert; display patient contact information or demographic data; and/or display special notes (e.g., see column 510). A clinician can respond to the alert by selecting check boxes on the dashboard screen, for example, corresponding to an appropriate action or intervention (e.g., call patient, call physician, etc.) The clinician can also be allowed to type documentation notes into the dashboard screen. Once the clinician completes the screen, an indicator such as column 512 can be configured to display what action has been scheduled or ordered. In certain embodiments, the clinician may also have the option to select a false positive status that enables the system 122 to perform a progressive adjustment to the personalized patient activity signature.

In various embodiments, one or more different types of users may access or communicate with the system 122 through a variety of access devices. Examples of such access devices may include, without limitation, desktop computers, laptops, notebooks, mobile devices (e.g., phones, smart phones, tablets, etc.), or many other types of computing devices or computer systems. Communications which occur between or among the system 122, patients 102, and/or various other users may be conducted through one or more kinds of communication media 132, such as networked media 132A, wireless media 132B, and/or wireline connections 132C.

In various embodiments of the invention, it can be seen that a combination of a wearable multi-sensor motion detection device and data analytics may be utilized to provide early detection or warning of new symptoms or disease exacerbation through analysis of deviations in progressively refined patterns of motion embodied as a personalized activity signature.

In one example of the application of certain embodiments of the invention, a 39-year-old diabetic woman typically walks approximately one to two miles each afternoon between 1:00 p.m. and 3:00 p.m. as part of her routine exercise regimen. During the day, she normally walks another half mile total. This morning she is not feeling well. After awakening at 10:00 a.m. (typically 8:30 a.m.), she fails to walk during the afternoon and only travels back and forth to the bathroom four times that day. Various aspects of the present system can be programmed to detect a multi-variable deviation from her motion signature profile or patient activity signature in terms of: time of awakening, total distance traveled, and failure to walk during the afternoon. This triggers a warning on a networked-based disease exacerbation dashboard, and as a result the care coordination team calls to check on her that afternoon. She is prompted to take a glucometer reading and her blood glucose level is noted to be 495. Instructions are provided to the patient and a home health assessment is arranged.

In another example of the application of certain embodiments of the invention, during a routine follow-up, a 67-year-old patient with congestive heart failure (CHF) tells his physician that he is following his diet and is limiting salt intake. Three days later, he experiences worsening dyspnea (difficulty breathing) and cannot lie flat in bed. While he normally awakens twice during sleep to urinate, he awakens and walks to his living room four times that evening. He returns to bed at 5:00 a.m. and awakens for the day at 6:30 a.m. He normally walks the distance of his driveway to pick up the morning newspaper, but fails to do so this morning. His ankles are swollen, yet he does not alert his healthcare team. The present system can be programmed to detect a multi-variable deviation from his motion signature profile or patient activity signature in terms of: multiple night time awakenings, early morning awakening, and failure to walk the length of his driveway to pick up the newspaper. This triggers a warning on the dashboard, and as a result his care coordination nurse calls and discovers that his ankles are swollen, he has gained 11 pounds of fluid, and that he cannot catch his breath. This triggers an urgent visit to his home, where intravenous diuretics are administered for a CHF exacerbation.

In another example of the application of certain embodiments of the invention, a 47-year-old woman with end-stage renal disease presents to dialysis three times each week (Monday, Wednesday, and Friday). On those days, she is routinely less active. On the weekend, she typically visits her grandchildren and walks with them in the neighborhood park. This Sunday however, she awakens at 10:00 a.m. (typically 8:00-8:30 a.m.) and does not leave her bedroom more than once. The present system can be programmed to detect a multi-variable deviation from her motion signature profile or patient activity signature in terms of late awakening and diminished ambulation. This triggers a warning on the dashboard, and a call from her care coordinator elicits from her that she is feeling dizzy. She also reports not having visited her grandchildren. She is prompted to visit a local urgent care facility, and an element of confusion is noted. Multiple electrolyte abnormalities are detected and she subsequently receives dialysis treatment.

In another example of the application of certain embodiments of the invention, a 78-year-old man never misses his exercise class held on Tuesdays and Thursdays. This morning he awakens at 8:00 a.m., prepares breakfast and walks around the block as he does each morning. Halfway though his walk, his gait slows considerably. He does not show up for the exercise class. The present system can be programmed to detect a multi-variable deviation from his motion signature profile or patient activity signature in terms of: ambulatory slowing and no exercise registered between the hours of 10:30-11:30 a.m. when he otherwise routinely participates in his exercise class. This prompts a call from his care coordinator who notes slurring of speech. She immediately calls 911, an ambulance is dispatched, and the patient is admitted to the hospital with an acute stroke.

In another example of the application of certain embodiments of the invention, it is 11:00 a.m. and a 74-year-old woman with rheumatoid arthritis has not arisen from bed. She normally eats breakfast at 8:00 a.m. No motion has been detected after 3:00 a.m. when she normally awakens to urinate. The present system can be programmed to detect a deviation from her motion signature profile or patient activity signature in terms of no evidence of movement three hours past her typical time of awakening. This prompts a call from her care coordinator, but the patient does not answer the phone. The ambulance crew finds her on the floor in her bedroom, unable to ambulate. The patient fell, experienced a hip fracture and could not reach the phone.

In each of these scenarios, an alert is provider to a care coordinator who calls the patient and discovers a health challenge that might otherwise be undetected. While false positives may occur, the cost of a phone call is outweighed by the significant potential for early intervention. By developing an individualized motion signature profile or patient activity signature through a progressive series of machine learning algorithms, it becomes apparent that simple changes in multiple activity patterns can serve as an early warning system for disease exacerbation, or a change in health status. As a direct result, care can be instituted with potential life-saving impact, and improved care experiences can be realized and often at a lower cost than other approaches.

The examples presented herein are intended to illustrate potential and specific implementations of the present invention. It can be appreciated that the examples are intended primarily for purposes of illustration of the invention for those skilled in the art. No particular aspect or aspects of the examples are necessarily intended to limit the scope of the present invention. For example, no particular aspect or aspects of the examples of system architectures, user interface layouts, or screen displays described herein are necessarily intended to limit the scope of the invention.

It is to be understood that the figures and descriptions of the present invention have been simplified to illustrate elements that are relevant for a clear understanding of the present invention, while eliminating, for purposes of clarity, other elements. Those of ordinary skill in the art will recognize, however, that a sufficient understanding of the present invention can be gained by the present disclosure, and therefore, a more detailed description of such elements is not provided herein.

Any element expressed herein as a means for performing a specified function is intended to encompass any way of performing that function including, for example, a combination of elements that performs that function. Furthermore the invention, as may be defined by such means-plus-function claims, resides in the fact that the functionalities provided by the various recited means are combined and brought together in a manner as defined by the appended claims. Therefore, any means that can provide such functionalities may be considered equivalents to the means shown herein.

In various embodiments, modules or software can be used to practice certain aspects of the invention. For example, software-as-a-service (SaaS) models or application service provider (ASP) models may be employed as software application delivery models to communicate software applications to clients or other users. Such software applications can be downloaded through an Internet connection, for example, and operated either independently (e.g., downloaded to a laptop or desktop computer system) or through a third-party service provider (e.g., accessed through a third-party web site). In addition, cloud computing techniques may be employed in connection with various embodiments of the invention. In certain embodiments, a "module" may include software, firmware, hardware, or any reasonable combination thereof.

Moreover, the processes associated with the present embodiments may be executed by programmable equipment, such as computers. Software or other sets of instructions that may be employed to cause programmable equipment to execute the processes may be stored in any storage device, such as a computer system (non-volatile) memory. Furthermore, some of the processes may be programmed when the computer system is manufactured or via a computer-readable memory storage medium.

It can also be appreciated that certain process aspects described herein may be performed using instructions stored on a computer-readable memory medium or media that direct a computer or computer system to perform process steps. A computer-readable medium may include, for example, memory devices such as diskettes, compact discs of both read-only and read/write varieties, optical disk drives, and hard disk drives. A computer-readable medium may also include memory storage that may be physical, virtual, permanent, temporary, semi-permanent and/or semi-temporary. Memory and/or storage components may be implemented using any computer-readable media capable of storing data such as volatile or non-volatile memory, removable or non-removable memory, erasable or non-erasable memory, writeable or re-writeable memory, and so forth. Examples of computer-readable storage media may include, without limitation, RAM, dynamic RAM (DRAM), Double-Data-Rate DRAM (DDRAM), synchronous DRAM (SDRAM), static RAM (SRAM), read-only memory (ROM), programmable ROM (PROM), erasable programmable ROM (EPROM), electrically erasable programmable ROM (EEPROM), flash memory (e.g., NOR or NAND flash memory), content addressable memory (CAM), polymer memory (e.g., ferroelectric polymer memory), phase-change memory, ovonic memory, ferroelectric memory, silicon-oxide-nitride-oxide-silicon (SONOS) memory, magnetic or optical cards, or any other type of media suitable for storing information.

A "computer," "computer system," "computing apparatus," "component," or "computer processor" may be, for example and without limitation, a processor, microcomputer, minicomputer, server, mainframe, laptop, personal data assistant (PDA), wireless e-mail device, smart phone, mobile phone, electronic tablet, cellular phone, pager, processor, fax machine, scanner, or any other programmable device or computer apparatus configured to transmit, process, and/or receive data. Computer systems and computer-based devices disclosed herein may include memory and/or storage components for storing certain software applications used in obtaining, processing, and communicating information. It can be appreciated that such memory may be internal or external with respect to operation of the disclosed embodiments. In various embodiments, a "host," "engine," "loader," "filter," "platform," or "component" may include various computers or computer systems, or may include a reasonable combination of software, firmware, and/or hardware.

In various embodiments of the present invention, a single component may be replaced by multiple components, and multiple components may be replaced by a single component, to perform a given function or functions. Except where such substitution would not be operative to practice embodiments of the present invention, such substitution is within the scope of the present invention. Any of the servers described herein, for example, may be replaced by a "server farm" or other grouping of networked servers (e.g., a group of server blades) that are located and configured for cooperative functions. It can be appreciated that a server farm may serve to distribute workload between/among individual components of the farm and may expedite computing processes by harnessing the collective and cooperative power of multiple servers. Such server farms may employ load-balancing software that accomplishes tasks such as, for example, tracking demand for processing power from different machines, prioritizing and scheduling tasks based on network demand, and/or providing backup contingency in the event of component failure or reduction in operability.

In general, it will be apparent to one of ordinary skill in the art that various embodiments described herein, or components or parts thereof, may be implemented in many different embodiments of software, firmware, and/or hardware, or modules thereof. The software code or specialized control hardware used to implement some of the present embodiments is not limiting of the present invention. For example, the embodiments described hereinabove may be implemented in computer software using any suitable computer programming language such as .NET, SQL, MySQL, or HTML using, for example, conventional or object-oriented techniques. Programming languages for computer software and other computer-implemented instructions may be translated into machine language by a compiler or an assembler before execution and/or may be translated directly at run time by an interpreter. Examples of assembly languages include ARM, MIPS, and x86; examples of high level languages include Ada, BASIC, C, C++, C#, COBOL, Fortran, Java, Lisp, Pascal, Object Pascal; and examples of scripting languages include Bourne script, JavaScript, Python, Ruby, PHP, and Perl. Various embodiments may be employed in a Lotus Notes environment, for example. Such software may be stored on any type of suitable computer-readable medium or media such as, for example, a magnetic or optical storage medium. Thus, the operation and behavior of the embodiments are described without specific reference to the actual software code or specialized hardware components. The absence of such specific references is feasible because it is clearly understood that artisans of ordinary skill would be able to design software and control hardware to implement the embodiments of the present invention based on the description herein with only a reasonable effort and without undue experimentation.

Various embodiments of the systems and methods described herein may employ one or more electronic computer networks to promote communication among different components, transfer data, or to share resources and information. Such computer networks can be classified according to the hardware and software technology that is used to interconnect the devices in the network, such as optical fiber, Ethernet, wireless LAN, HomePNA, power line communication or G.hn. The computer networks may also be embodied as one or more of the following types of networks: local area network (LAN); metropolitan area network (MAN); wide area network (WAN); virtual private network (VPN); storage area network (SAN); or global area network (GAN), among other network varieties.

For example, a WAN computer network may cover a broad area by linking communications across metropolitan, regional, or national boundaries. The network may use routers and/or public communication links. One type of data communication network may cover a relatively broad geographic area (e.g., city-to-city or country-to-country) which uses transmission facilities provided by common carriers, such as telephone service providers. In another example, a GAN computer network may support mobile communications across multiple wireless LANs or satellite networks. In another example, a VPN computer network may include links between nodes carried by open connections or virtual circuits in another network (e.g., the Internet) instead of by physical wires. The link-layer protocols of the VPN can be tunneled through the other network. One VPN application can promote secure communications through the Internet. The VPN can also be used to separately and securely conduct the traffic of different user communities over an underlying network. The VPN may provide users with the virtual experience of accessing the network through an IP address location other than the actual IP address which connects the access device to the network.

The computer network may be characterized based on functional relationships among the elements or components of the network, such as active networking, client-server, or peer-to-peer functional architecture. The computer network may be classified according to network topology, such as bus network, star network, ring network, mesh network, star-bus network, or hierarchical topology network, for example. The computer network may also be classified based on the method employed for data communication, such as digital and analog networks.

Embodiments of the methods and systems described herein may employ internetworking for connecting two or more distinct electronic computer networks or network segments through a common routing technology. The type of internetwork employed may depend on administration and/or participation in the internetwork. Non-limiting examples of internetworks include intranet, extranet, and Internet. Intranets and extranets may or may not have connections to the Internet. If connected to the Internet, the intranet or extranet may be protected with appropriate authentication technology or other security measures. As applied herein, an intranet can be a group of networks which employ Internet Protocol, web browsers and/or file transfer applications, under common control by an administrative entity. Such an administrative entity could restrict access to the intranet to only authorized users, for example, or another internal network of an organization or commercial entity. As applied herein, an extranet may include a network or internetwork generally limited to a primary organization or entity, but which also has limited connections to the networks of one or more other trusted organizations or entities (e.g., customers of an entity may be given access an intranet of the entity thereby creating an extranet).

Computer networks may include hardware elements to interconnect network nodes, such as network interface cards (NICs) or Ethernet cards, repeaters, bridges, hubs, switches, routers, and other like components. Such elements may be physically wired for communication and/or data connections may be provided with microwave links (e.g., IEEE 802.12) or fiber optics, for example. A network card, network adapter or NIC can be designed to allow computers to communicate over the computer network by providing physical access to a network and an addressing system through the use of MAC addresses, for example. A repeater can be embodied as an electronic device that receives and retransmits a communicated signal at a boosted power level to allow the signal to cover a telecommunication distance with reduced degradation. A network bridge can be configured to connect multiple network segments at the data link layer of a computer network while learning which addresses can be reached through which specific ports of the network. In the network, the bridge may associate a port with an address and then send traffic for that address only to that port. In various embodiments, local bridges may be employed to directly connect local area networks (LANs); remote bridges can be used to create a wide area network (WAN) link between LANs; and/or, wireless bridges can be used to connect LANs and/or to connect remote stations to LANs.

In various embodiments, a hub may be employed which contains multiple ports. For example, when a data packet arrives at one port of a hub, the packet can be copied unmodified to all ports of the hub for transmission. A network switch or other devices that forward and filter OSI layer 2 datagrams between ports based on MAC addresses in data packets can also be used. A switch can possess multiple ports, such that most of the network is connected directly to the switch, or another switch that is in turn connected to a switch. The term "switch" can also include routers and bridges, as well as other devices that distribute data traffic by application content (e.g., a Web URL identifier). Switches may operate at one or more OSI model layers, including physical, data link, network, or transport (i.e., end-to-end). A device that operates simultaneously at more than one of these layers can be considered a multilayer switch. In certain embodiments, routers or other like networking devices may be used to forward data packets between networks using headers and forwarding tables to determine an optimum path through which to transmit the packets.

As employed herein, an application server may be a server that hosts an API to expose business logic and business processes for use by other applications. Examples of application servers include J2EE or Java EE 5 application servers including WebSphere Application Server. Other examples include WebSphere Application Server Community Edition (IBM), Sybase Enterprise Application Server (Sybase Inc), WebLogic Server (BEA), JBoss (Red Hat), JRun (Adobe Systems), Apache Geronimo (Apache Software Foundation), Oracle OC4J (Oracle Corporation), Sun Java System Application Server (Sun Microsystems), and SAP Netweaver AS (ABAP/Java). Also, application servers may be provided in accordance with the .NET framework, including the Windows Communication Foundation, .NET Remoting, ADO.NET, and ASP.NET among several other components. For example, a Java Server Page (JSP) is a servlet that executes in a web container which is functionally equivalent to CGI scripts. JSPs can be used to create HTML pages by embedding references to the server logic within the page. The application servers may mainly serve web-based applications, while other servers can perform as session initiation protocol servers, for instance, or work with telephony networks. Specifications for enterprise application integration and service-oriented architecture can be designed to connect many different computer network elements. Such specifications include Business Application Programming Interface, Web Services Interoperability, and Java EE Connector Architecture.

Embodiments of the methods and systems described herein may divide functions between separate CPUs, creating a multiprocessing configuration. For example, multiprocessor and multi-core (multiple CPUs on a single integrated circuit) computer systems with co-processing capabilities may be employed. Also, multitasking may be employed as a computer processing technique to handle simultaneous execution of multiple computer programs.

In various embodiments, the computer systems, data storage media, or modules described herein may be configured and/or programmed to include one or more of the above-described electronic, computer-based elements and components, or computer architecture. In addition, these elements and components may be particularly configured to execute the various rules, algorithms, programs, processes, and method steps described herein.

Various embodiments may be described herein in the general context of computer executable instructions, such as software, program modules, and/or engines being executed by a computer. Generally, software, program modules, and/or engines include any software element arranged to perform particular operations or implement particular abstract data types. Software, program modules, and/or engines can include routines, programs, objects, components, data structures and the like that perform particular tasks or implement particular abstract data types. An implementation of the software, program modules, and/or engines components and techniques may be stored on and/or transmitted across some form of computer-readable media. In this regard, computer-readable media can be any available medium or media useable to store information and accessible by a computing device. Some embodiments also may be practiced in distributed computing environments where operations are performed by one or more remote processing devices that are linked through a communications network. In a distributed computing environment, software, program modules, and/or engines may be located in both local and remote computer storage media including memory storage devices.

Although some embodiments may be illustrated and described as comprising functional components, software, engines, and/or modules performing various operations, it can be appreciated that such components or modules may be implemented by one or more hardware components, software components, and/or combination thereof. The functional components, software, engines, and/or modules may be implemented, for example, by logic (e.g., instructions, data, and/or code) to be executed by a logic device (e.g., processor). Such logic may be stored internally or externally to a logic device on one or more types of computer-readable storage media. In other embodiments, the functional components such as software, engines, and/or modules may be implemented by hardware elements that may include processors, microprocessors, circuits, circuit elements (e.g., transistors, resistors, capacitors, inductors, and so forth), integrated circuits, application specific integrated circuits (ASIC), programmable logic devices (PLD), digital signal processors (DSP), field programmable gate array (FPGA), logic gates, registers, semiconductor device, chips, microchips, chip sets, and so forth.

Examples of software, engines, and/or modules may include software components, programs, applications, computer programs, application programs, system programs, machine programs, operating system software, middleware, firmware, software modules, routines, subroutines, functions, methods, procedures, software interfaces, application program interfaces (API), instruction sets, computing code, computer code, code segments, computer code segments, words, values, symbols, or any combination thereof. Determining whether an embodiment is implemented using hardware elements and/or software elements may vary in accordance with any number of factors, such as desired computational rate, power levels, heat tolerances, processing cycle budget, input data rates, output data rates, memory resources, data bus speeds and other design or performance constraints.

In some cases, various embodiments may be implemented as an article of manufacture. The article of manufacture may include a computer readable storage medium arranged to store logic, instructions and/or data for performing various operations of one or more embodiments. In various embodiments, for example, the article of manufacture may comprise a magnetic disk, optical disk, flash memory or firmware containing computer program instructions suitable for execution by a general purpose processor or application specific processor. The embodiments, however, are not limited in this context.

Additionally, it is to be appreciated that the embodiments described herein illustrate example implementations, and that the functional elements, logical blocks, modules, and circuits elements may be implemented in various other ways which are consistent with the described embodiments. Furthermore, the operations performed by such functional elements, logical blocks, modules, and circuits elements may be combined and/or separated for a given implementation and may be performed by a greater number or fewer number of components or modules. As will be apparent to those of skill in the art upon reading the present disclosure, each of the individual embodiments described and illustrated herein has discrete components and features which may be readily separated from or combined with the features of any of the other several aspects without departing from the scope of the present disclosure. Any recited method can be carried out in the order of events recited or in any other order which is logically possible.

Unless specifically stated otherwise, it may be appreciated that terms such as "processing," "computing," "calculating," "determining," or the like, refer to the action and/or processes of a computer or computing system, or similar electronic computing device, such as a general purpose processor, a DSP, ASIC, FPGA or other programmable logic device, discrete gate or transistor logic, discrete hardware components, or any combination thereof designed to perform the functions described herein that manipulates and/or transforms data represented as physical quantities (e.g., electronic) within registers and/or memories into other data similarly represented as physical quantities within the memories, registers or other such information storage, transmission or display devices.

Certain embodiments may be described using the expression "coupled" and "connected" along with their derivatives. These terms are not necessarily intended as synonyms for each other. For example, some embodiments may be described using the terms "connected" and/or "coupled" to indicate that two or more elements are in direct physical or electrical contact with each other. The term "coupled," however, also may mean that two or more elements are not in direct contact with each other, but yet still co-operate or interact with each other. With respect to software elements, for example, the term "coupled" may refer to interfaces, message interfaces, application program interface (API), exchanging messages, and so forth.

It will be appreciated that those skilled in the art will be able to devise various arrangements which, although not explicitly described or shown herein, embody the principles of the present disclosure and are comprised within the scope thereof. Furthermore, all examples and conditional language recited herein are principally intended to aid the reader in understanding the principles described in the present disclosure and the concepts contributed to furthering the art, and are to be construed as being without limitation to such specifically recited examples and conditions. Moreover, all statements herein reciting principles, aspects, and embodiments as well as specific examples thereof, are intended to encompass both structural and functional equivalents thereof. Additionally, it is intended that such equivalents comprise both currently known equivalents and equivalents developed in the future, i.e., any elements developed that perform the same function, regardless of structure. The scope of the present disclosure, therefore, is not intended to be limited to the exemplary aspects and aspects shown and described herein.

The terms "a" and "an" and "the" and similar referents used in the context of the present disclosure (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as when it were individually recited herein. All methods described herein can be performed in any suitable order unless otherwise indicated herein or otherwise clearly contradicted by context. The use of any and all examples, or exemplary language (e.g., "such as," "in the case," "by way of example") provided herein is intended merely to better illuminate the disclosed embodiments and does not pose a limitation on the scope otherwise claimed. No language in the specification should be construed as indicating any non-claimed element essential to the practice of the claimed subject matter. It is further noted that the claims may be drafted to exclude any optional element. As such, this statement is intended to serve as antecedent basis for use of such exclusive terminology as solely, only and the like in connection with the recitation of claim elements, or use of a negative limitation.

Groupings of alternative elements or embodiments disclosed herein are not to be construed as limitations. Each group member may be referred to and claimed individually or in any combination with other members of the group or other elements found herein. It is anticipated that one or more members of a group may be comprised in, or deleted from, a group for reasons of convenience and/or patentability. Reference to "one embodiment" or "an embodiment" means that a particular feature, structure, or characteristic described in connection with the embodiment is comprised in at least one embodiment. The appearances of the phrase "in one embodiment" or "in one aspect" in the specification are not necessarily all referring to the same embodiment.

While various embodiments of the invention have been described herein, it should be apparent, however, that various modifications, alterations and adaptations to those embodiments may occur to persons skilled in the art with the attainment of some or all of the advantages of the present invention. The disclosed embodiments are therefore intended to include all such modifications, alterations and adaptations without departing from the scope and spirit of the present invention as described and claimed herein.

What is claimed is:

1. A method for analyzing a condition of a patient:
   generating, by an electronic computer processor, at least one progressively established patient activity signature in connection with previously observed activity or movement of a patient derived at least in part from at least one electronic sensor;
   collecting, by the processor, current movement data associated with the patient;
   comparing, by the processor, the current patient movement data against the at least one progressively established patient activity signature; and,
   generating, by the processor, at least one notification in association with comparing the current patient movement data to the at least one progressively established patient activity signature.

2. The method of claim 1, further comprising detecting, by the processor, at least one deviation from the at least one progressively established patient activity signature.

3. The method of claim 2, further comprising communicating an alert to at least one health care provider in response to the detected deviation in the at least one progressively established patient activity signature.

4. The method of claim 3, further comprising communicating the alert with at least one dashboard screen.

5. The method of claim 1, further comprising receiving, by the processor, data representative of movement or activity of the patient from an activity detection device.

6. The method of claim 5, wherein the activity detection device comprises at least one of a motion sensor, a tilt sensor, an inertia sensor, a global positioning system, an accelerometer, or a reasonable combination thereof.

7. The method of claim 5, wherein the activity detection device comprises a wireless-enabled device.

8. The method of claim 7, wherein the device comprises a wireless transmitter structured for sending data to a relay station.

9. The method of claim 1, further comprising receiving, by the processor, data associated with the at least one progressively established patient activity in a data analytics module.

10. The method of claim 9, further comprising operatively associating the data analytics module with a machine learning module programmed for determining at least one pattern associated with behavior of the patient.

11. The method of claim 1, further comprising quantifying motion of the patient in terms of at least one of magnitude, duration, frequency, temporal occurrence, or a combination thereof.

12. The method of claim 11, further comprising plotting the quantified motion over time to create a graphical representation of a spectrum of activity for the patient.

13. A system for analyzing a condition of a patient:
an electronic computer processor programmed for executing instructions associated with at least one module;
a data analytics module programmed for generating at least one progressively established patient activity signature in connection with previously observed activity or movement of a patient derived at least in part from at least one electronic sensor;
a patient activity monitoring module programmed for collecting current movement data associated with the patient;
wherein the data analytics module is programmed for comparing the current patient movement data against the at least one progressively established patient activity signature; and,
an alert notification module programmed for generating at least one notification in association with comparing the current patient movement data to the at least one progressively established patient activity signature.

14. The system of claim 13, further comprising the data analytics module programmed for detecting at least one deviation from the at least one progressively established patient activity signature.

15. The system of claim 13, further comprising the alert notification module programmed for communicating an alert to at least one health care provider in response to the detected deviation in the at least one progressively established.

16. The system of claim 13, further comprising the patient activity monitoring module programmed for receiving data representative of movement or activity of the patient from an activity detection device.

17. The system of claim 16, wherein the activity detection device comprises at least one of a motion sensor, a tilt sensor, an inertia sensor, a global positioning system, an accelerometer, or a reasonable combination thereof.

18. The system of claim 16, wherein the activity detection device comprises a wireless-enabled device.

19. The system of claim 18, wherein the device comprises a wireless transmitter structured for sending data to a relay station.

20. The system of claim 13, further comprising a machine learning module programmed for determining at least one pattern associated with behavior of the patient.

21. The system of claim 13, further comprising the data analytics module programmed to quantify motion of the patient in terms of at least one of magnitude, duration, frequency, temporal occurrence, or a combination thereof.

22. The system of claim 21, further comprising a module programmed for plotting the quantified motion over time to create a graphical representation of a spectrum of activity for the patient.

* * * * *